United States Patent [19]

Meares et al.

[11] Patent Number: 4,722,892

[45] Date of Patent: Feb. 2, 1988

[54] MONOCLONAL ANTIBODIES AGAINST METAL CHELATES

[76] Inventors: Claude F. Meares, 3310 Trawler Pl., Davis, Calif. 95616; Gary S. David, 9477 Poole St., La Jolla, Calif. 92037

[21] Appl. No.: 646,602

[22] Filed: Aug. 31, 1984

[51] Int. Cl.$^4$ ........................................... G01N 33/577
[52] U.S. Cl. ........................................ 435/7; 424/85; 436/73; 436/81; 436/548; 436/813; 530/387; 530/808; 935/110
[58] Field of Search ................. 260/112 B, 112 R; 424/85; 436/512, 519, 547, 548, 813, 73, 81; 435/7; 530/387, 808; 935/110

[56] References Cited

U.S. PATENT DOCUMENTS 4,472,509  9/1984  Gansow ........................ 436/819 X
4,474,893 10/1984  Reading ........................ 436/548 X

OTHER PUBLICATIONS

Scheinberg, D. A. et al., Science, 215 (4539), 1511–1513 (Mar. 19, 1982).
Chemical Abstracts, 100:205818c (1984).
Buckley, R. G. et al., Febs Letters, 166 (1) 202–204 (Jan. 23, 1984).
Powe, J. et al., Cancer Drug Delivery, 1(2), 125–135 (1984).

Primary Examiner—Sidney Marantz

[57] ABSTRACT

Monoclonal Antibodies which are specific for a complex of a chelating agent and a metallic ion are described. The antibody has an association constant ($K_a$) for the complex which is at least about ten times greater than the $K_a$ for the chelating agent alone or its complex with another metal.

13 Claims, No Drawings

MONOCLONAL ANTIBODIES AGAINST METAL CHELATES

FIELD OF THE INVENTION

This invention relates to monoclonal antibodies. In another apsect it relates to metal-ion complexes with chelating agents. In yet another aspect, it relates to applications of monoclonal antibodies for diagnostic and therapeutic uses.

BACKGROUND

Monoclonal antibodies are becoming increasingly important tools for the diagnosis or treatment of diseases or other physical conditions. They also show promise in industrial applications, for example, for the purification of commercially valuable materials found in mixtures difficult to resolve by other than affinity purification.

For these applications, the antibody is selected based upon its ability to bind an antigen. In certain applications the antibody may be used without modification. For example, passive therapeutic treatments use unmodified antibody. Most applications, however, including those with the most current commercial significance, use an antibody that has been modified in some way. Thus, the antibody may be bound to a solid phase and used as an immunoadsorbent in affinity purification or immunometric assays.

In other applications the antibody may be labeled with, for example, a radionuclide for use in detecting antigens in diagnostic assays and for in vivo imaging. An antibody labeled with a radionuclide, drug or toxin can have therapeutic applications.

The ability to label monoclonal antibodies is complicated in that each such antibody, being a discrete chemical compound, exhibits its own labeling idiosyncracies. Therefore, the ability to label efficiently and simply is highly desirable.

In that regard, we have proposed to label monoclonal antibodies with metallic radionuclides by the use of a chelating agent for the metal. The chelating agent is first conjugated with the monoclonal antibody of choice. Since the same chelating agent may bind a number of different metals, it is only necessary to work out the chemical protocol for optimal binding of the antibody to the chelating agent in order to be able to label the antibody with any of the several radionuclides which the chelating agent will bind. While this procedure has greatly simplified the labeling of monoclonal antibodies with radionuclides, it is still necessary to determine the optimal binding conditions for each combination of antibody and chelating agent.

SUMMARY OF THE INVENTION

We have discovered that monoclonal antibodies can be obtained that, surprisingly, exhibit the ability of being able to bind preferentially to a complex of a chelating agent and a specific metal as compared to its ability to bind with either the chelating agent itself or with a complex of the chelating agent with another metal. For example, we have obtained a monoclonal antibody using a chelate complex of In(III) and (L)-aminobenzylethylenediaminetetraacetic acid (aminobenzyl EDTA) bound to keyhole limpet hemocyanin as an immunogen which has an affinity for the In(III)-chelate complex ($K_A$) of greater than $10^9 M^{-1}$. By comparison, the antibody demonstrated a substantially lower affinity ($K_A = 10^8 M^{-1}$ or less) for L-aminobenzyl EDTA complexes of other metal ions.

Antibodies which exhibit this specificity for a chelate complex are useful for the conjugation of radionuclides to antibodies, for the purification of trace metals and in other applications described hereinafter.

DESCRIPTION OF PREFERRED EMBODIMENTS

As pointed out above, the present invention provides monoclonal antibodies which exhibit specificity for the complex of a chelating agent and a specific metal as compared to the chelating agent itself or a complex of the agent with another metal. As used herein, a monoclonal antibody is considered to exhibit specificity for a complex of a specific metal and chelating agent when the binding constant ($K_A$) between the antibody and complex is an order of magnitude (ten times) greater than the $K_A$ of the antibody for the chelating agent alone or for a complex of the chelating agent with another metal. Chelating agents useful in the invention are disclosed in Adams et al., Ser. No. 315,286 filed Oct. 27, 1981, the disclosure of which is incorporated by reference. The following experiments illustrate the present invention using an In(III) chelate of L-aminobenzyl EDTA as a hapten.

EXAMPLE I

PREPARATION OF COMPLEX OF In(III) AND L-AMINOBENZYL EDTA

Keyhole limpet hemocyanin (9.3 mg) was allowed to react in 265 μl of an aqueous solution (pH 9) with (L)—SCN—$C_6H_4$—$CH_2$ EDTA at 36° C. for 8 hr. The resulting solution was mixed with 90 μl of 0.1 M indium citrate and dialyzed against 1 mM EDTA, 0.15 M NaCl. From the absorbance of the thiourea group at 310 nm it was determined that there was approximately 0.1 mg of attached chelate per mg of protein.

EXAMPLE II

MONOCLONAL ANTIBODY PREPARATION

Antibody producing hybridoma cell lines were prepared as follows. Spleen cells from BALB/c mice multiply immunized with the antigen described above were fused with a variant of the P3.653 myeloma cell line. See Gerhard, *Monoclonal Antibodies*, Edited by Kennett et al., Plenum Press, New York (1980). The resulting hybridomas were screened by a solid phase second antibody radioimmunoassay for their ability to bind $^{111}$In-aminobenzyl-EDTA (Wang et al., *Journal of Immunological Methods*, 18, 157, 1977). Based on their high titers and relatively high affinity as determined by inhibition of binding by unlabeled antigen, two antibodies designated by us as CHA255 and CHB235 were chosen for further study and injected intraperitoneally into BALB/c mice for ascites production. The monoclonal antibodies were purified from mouse ascites by ion-exchange chromatography on DEAE-cellulose as described by Parham et al., *J. Immunol. Meth.*, 53, 133 (1982).

EXAMPLE III

DETERMINATION OF ASSOCIATION CONSTANTS

Table I below sets forth the association constants of the two monoclonal antibodies described in Example II for a number of chelates. In Part A, the relative affinities of the antibodies for aminobenzyl EDTA complexes of In(III) and other ions are shown. In Part B, the binding constants of the antibodies for In(III) complexes with other chelating agents are shown. The metals selected for comparison were trivalent ions similar to In(III) and divalent ions whose EDTA complexes form structures similar to that of an In-EDTA complex. The binding constants for the chelates were determined by the method of Eisen, *Meth. Med. Res.*, 10, 106 (1964) by dialysis of the antibody and metal chelates to near equilibrium (24h) at 37° in 0.05M 2-hydroxyethyl-piperazine-ethanesulfonate, 0.1M NaCl, 0.1% $NaN_3$ and 0.1% bovine serum albumin at pH 7. The concentration of antibody binding sites inside the dialysis bag was $10^{-7}$ M, and the concentration of free In(III)-(L)-aminobenzyl EDTA was in the same range.

Known amounts of another chelate were added to the solution after equilibrium until roughly half of the bound indium chelate had been displaced at equilibrium.

TABLE 1

Relative Properties of Metal Chelates

A. Chelates of L-Benzyl-EDTA with Different Metal Ions

| Metals | $r_{ion}^{(A)}$ | log $K_S^{EDTA(M)}$ | $K_A^{CHA255}$ | $K_A^{CHB235}$ |
|---|---|---|---|---|
| In(III) | 0.81 | 25.0 | $4.0 \times 10^9 (\pm 6.9\%)$ | $1.1 \times 10^8 (\pm 7.9\%)$ |
| Sc(III) | 0.81 | 23.1 | $3.0 \times 10^6 (\pm 13\%)$ | $4.6 \times 10^4 (\pm 39\%)$ |
| Fe(III) | 0.64 | 25.1 | $1.8 \times 10^8 (\pm 13\%)$ | $2.4 \times 10^6 (\pm 18\%)$ |
| Ga(III) | 0.62 | 20.3 | $4.8 \times 10^5 (\pm 45\%)$ | $5.2 \times 10^4 (\pm 16\%)$ |
| Tb(III) | 1.00 | 17.9 | $1.2 \times 10^6 (\pm 12\%)$ | $2.7 \times 10^4 (\pm 15\%)$ |
| Yb(III) | 0.94 | 19.5 | $1.1 \times 10^6 (\pm 20\%)$ | $2 \times 10^4 (\pm 90\%)$ |
| Mn(II) | 0.80 | 13.9 | $2.8 \times 10^6 (\pm 9.1\%)$ | $2.8 \times 10^4 (\pm 24\%)$ |
| Co(II) | 0.74 | 16.3 | $1.9 \times 10^6 (\pm 37)$ | $9.4 \times 10^4 (\pm 22\%)$ |
| Co(III) | 0.63 | 41.4 | $8.3 \times 10^5 (\pm 60\%)$ | $<1 \times 10^4$ |
| Cu(II) | 0.69 | 18.8 | $1.7 \times 10^6 (\pm 12\%)$ | $8.1 \times 10^4 (\pm 11\%)$ |
| Zn(II) | 0.74 | 16.5 | $1.4 \times 10^6 (\pm 14\%)$ | $3.5 \times 10^4 (\pm 27\%)$ |
| Cd(II) | 0.97 | 16.5 | $1.5 \times 10^7 (\pm 8.0\%)$ | $1.6 \times 10^5 (\pm 8.1\%)$ |

B. Indium Chelates with Different Chelators

| Chelator | $K_A^{CHA255}$ | $K_A^{CHA235}$ |
|---|---|---|
| L-Benzyl-EDTA | $4.0 \times 10^9 (\pm 6.9\%)$ | $1.1 \times 10^8 (\pm 7.9\%)$ |
| D-Benzyl-EDTA | $6.3 \times 10^7 (\pm 40\%)$ | $3.6 \times 10^7 (\pm 9.3\%)$ |
| EDTA | $1.7 \times 10^8 (8.3\%)$ | $1.3 \times 10^8 (\pm 13\%)$ |
| HED3A | $4.2 \times 10^7 (\pm 12\%)$ | $4.0 \times 10^7 (\pm 14\%)$ |

Table 1 Legend:
A: Column 1, the metals whose L-Benzyl-EDTA chelate (see FIG. 2) were tested against the indium chelate. Column 2, the ionic radius of each metal, in Angstroms (1A = $10^{-10}$m) according to Pauling, The Nature of the Chemical Bond, (3d Edition, Cornell University Press (1960). Column 3, the logarithm of the stability constant for each metal-EDTA chelate. (See Stability Constants of Metal Ion Complexes, L. G. Sillen and A. E. Martell, Editors, Chemical Society, London, 1964; Critical Stability Constants, A. E. Martell and R. M. Smith, Editors, Plenum, New York, 1974.) Columns 4 and 5, the antibody binding constants for each metal-L-Benzyl-EDTA chelate for the two different monoclonal antibodies studied. Coefficient of variation of each measurement given in parentheses.
B: Column 1, the different chelators used to make indium chelates. Columns 2 and 3, the antibody binding constants for each indium chelate.

The data in Table I, Part A, show that changing the metal in the chelate complex can result in a reduction of the $K_A$ by up to four (4) orders of magnitude. Although we do not wish to be bound to any particular theory, we believe the specificity exhibited by the antibody likely is the result of a direct interaction between the metal and the antibody.

The ability of the antibody to recognize the chelate complex of a specific ion relative to a complex of the chelating agent with another ion permits the detection and/or separation of metal ions from solutions containing other metals when the metal of choice forms a chelate. For example, trace metal analysis of water, pharmaceuticals or biological fluids can be accomplished by immunoassay. To achieve this, the chelating agent bound to a solid phase (for example aminobenzyl EDTA covalently bound to polystyrene, sepharose, polyacrylamide, could be used to extract the ion from a fluid of interest then, after separation of the fluid, the solid phase incubated in the usual way with a solution of an antibody against the chelate-metal ion complex labeled with an enzyme or other agent which permits detection of the labeled antibody. Radioactive labels, fluorescent labels and other labels applicable to immunoassays can also be used in place of an enzyme. After separation of unbound antibody, the presence of labeled antibody bound to the chelating agent indicates its presence in the fluid sample. Detecting and measuring the amount of either the bound or unbound antibody can be used to determine the amount of the ion in the sample of fluid.

Metals can be selectively removed from a fluid by adding the chelating agent to the fluid followed by extraction with the antibody bound to a solid phase.

A bifunctional monoclonal antibody obtained from a polydoma or by other means as described in copending application of Martinis et al., Ser. No. 367,784 filed Apr. 12, 1982now abandoned, the disclosure of which is incorporated by reference, having one specificity directed against a complex of a specific metal and chelating agent and the other against another antigen have utility. For example, such a bifunctional antibody having its other specificity against a tumor associated antigen can be used for in vivo tumor imaging or therapy by incorporating a radionuclide in the chelate. In such therapies, bifunctional antibody is infused and allowed to localize at the tumor site where the associated antigen it recognizes is located. The radionuclide-chelate complex is infused later. For example, if it is desired to image the tumor, preferably the radionuclide is selected on the basis of its emission of radiation, typically a $\gamma$-photon, which can be detected by photoscanning techniques. If it is desired to treat the tumor to reduce its size, preferably the radionuclide emits an electron or an alpha-particle.

After the second infusion of chelate, the complex that is not bound by the bifunctional antibody, being a small molecule, can be rapidly cleared from the body reducing the possibility of damage to non-tumor tissue.

The tumor associated antigens against which the bifunctional antibody may be targeted include, but are not limited to, alphafetoprotein, carcinoembryonic antigen, human choriogonadotropin, prostatic acid phosphatase and prostate specific antigen. Of the useful $\gamma$-emitting isotopes, 111In is preferred. Among the useful isotopes emitting an electron, 90y is preferred.

The ability of the antibody to recognize a radionuclidechelate complex reduces the need to develop complexes using a variety of chelating agents for multiple ion therapies. Thus, antibodies can be readily developed which distinguish between chelate complexes in which the radionuclides differ but the chelating agent is the same.

In another application, a bifunctional antibody, one of whose specificites is against a metal chelate and the other against a tumor associated antigen, can be infused and allowed to localize at the site of the tumor associated antigen. A toxin or drug to which is conjugated the metal chelate can be subsequently infused to be bound by the antibody at the tumor site. In this application, if the metal is a radionuclide that, upon decay, changes atomic number to a metal whose chelate is not bound tightly by the antibody, i.e., the $K_A$ for the chelate of the decay product is less than about $1 \times 10^7 \text{ M}^{-1}$ or, preferably, less than about $1 \times 10^6 \text{ M}^{-1}$, the antibody will release the chelate and the associated drug or toxin in the vicinity of the tumorous cell to facilitate its entry into the cell. In such a case, the radionuclide is selected to have a half-life which insures that release does not occur prematurely or over too long a period.

This ability of the antibody to recognize the chelate complex permits a plurality of drugs to be used with the same antibody by simply conjugating them to the same chelating agent, greatly simplifying the process of obtaining a panel of bifunctional antibodies having a specificity against a disease associated antigen and the other to a toxin or drug since the same chelating agent can be used to conjugate the toxins or drugs.

Those skilled in the art will appreciate that, whereas the above description has not expressly stated it to be the case, monoclonal antibody fragments including Fab and $Fab_2$ fragments can be used in place of the whole antibody except that an Fab fragment cannot be used by itself in those utilities which require a bifunctional antibody.

These and other advantages of the present invention will be apparent to those skilled in the art. Accordingly, the present invention is to be considered limited only by the appended claims.

We claim:

1. A monoclonal antibody which exhibits specificity for a complex comprising a chelating agent and a first metallic ion, the antibody having an association constant ($K_A$) for the complex at least about ten times greater than the $K_A$ of the antibody for the chelating agent itself or its complex with any other metallic ion.

2. A monoclonal antibody according to claim 1 wherein the metallic ion is a radionuclide.

3. A monoclonal antibody according to claims 1 or 2 wherein the monoclonal antibody is a bifunctional antibody, one specificity of which is against the complex of chelating agent and first metallic ion and the second against an antigen other than said complex.

4. A monoclonal antibody according to claim 3 wherein the second specificity is against a tumor associated antigen.

5. A monoclonal antibody according to claim 4 wherein the first metallic ion is a radionuclide whose product of radioactive decay is a metallic ion of a different atomic number and the $K_A$ of the antibody with the complex of decay product and chelating agent is less than about $1 \times 10^7 \text{ M}^{-1}$.

6. A monoclonal antibody according to claim 5 wherein the $K_A$ of the antibody and the complex of the decay product and the chelating agent is less than about $1 \times 10^6 \text{ M}^{-1}$.

7. A process for the treatment of a tumor having an antigen associated therewith comprising administering to a subject a monoclonal antibody according to claim 4 and allowing the antibody to localize at the situs of the tumor and then adminstering to the subject a composition comprising the chelate complex comprising the chelating agent and the first metallic ion, the metallic ion being a radionuclide that decays by emission of an electron or an alpha-particle.

8. A process according to claim 7 wherein the radionuclide is $^{90}Y$.

9. A process according to claim 7 wherein the chelating agent is conjugated with a chemotherapeutic agent and the radionuclide decays to a product having a different atomic number and the $K_A$ of the antibody with the complex of decay product and chelating agent is less than about $1 \times 10^7 \text{ M}^{-1}$.

10. A process according to claim 9 wherein the $K_A$ of the antibody with complex of decay product and chelating agent is less than about $1 \times 10^6 \text{ M}^{-1}$.

11. A process for the detection of a metal ion in a fluid comprising:
    (a) contacting the fluid with a chelating agent bound to a solid phase under conditions which will form a chelate complex with the metal;
    (b) separating the fluid from the solid phase;
    (c) contacting the solid phase with a monoclonal antibody according to claim 1 which antibody has a label which permits its presence to be detected and/or quantified;
    (d) separating unbound antibody from antibody bound to the complex;
    (e) detecting the labeled antibody bound to the chelate complex.

12. A process according to claim 11 wherein the amount of bound or unbound labeled antibody is determined and related to the concentration of ion in the fluid.

13. A process according to claim 11 or 12 wherein the label is a radioactive element, fluorescent element or an enzyme.

* * * * *